United States Patent
Brieva et al.

(10) Patent No.: US 11,446,233 B2
(45) Date of Patent: Sep. 20, 2022

(54) SERUMS FOR REDUCING LIPID PEROXIDATION

(71) Applicant: L'OREAL, Paris (FR)

(72) Inventors: Patricia Brieva, Manalapan, NJ (US); Stephen Matthew Lynch, Westfield, NJ (US); Maggie Su, Cranford, NJ (US); Madeline Jane Sverdlove, Jersey City, NJ (US); Ashleigh Nichole Murtaugh-Frey, Columbus, NJ (US); Angelike Galdi, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/038,977

(22) Filed: Sep. 30, 2020

(65) Prior Publication Data
US 2022/0096360 A1    Mar. 31, 2022

(51) Int. Cl.
| | |
|---|---|
| *A61K 36/00* | (2006.01) |
| *A61K 8/9789* | (2017.01) |
| *A61K 8/368* | (2006.01) |
| *A61K 8/67* | (2006.01) |
| *A61K 8/34* | (2006.01) |
| *A61Q 19/08* | (2006.01) |
| *A61K 8/365* | (2006.01) |

(52) U.S. Cl.
CPC ............ *A61K 8/9789* (2017.08); *A61K 8/345* (2013.01); *A61K 8/365* (2013.01); *A61K 8/368* (2013.01); *A61K 8/676* (2013.01); *A61Q 19/08* (2013.01); *A61K 2800/522* (2013.01)

(58) Field of Classification Search
CPC ... A61Q 19/08; A61K 2800/522; A61K 8/676
See application file for complete search history.

(56) References Cited

U.S. PATENT DOCUMENTS

2018/0116950 A1* 5/2018 Pan .................. A61K 8/678

OTHER PUBLICATIONS

Arcona, "Instant Magic Reversal Serum", Retrieved online <https://www.arcona.com/product/instant-magic-reversal-serum.html>, 6 pages, 2022.
Database GNPD [Online], Mintel, De Mamiel, UK, "Spring Facial Oil", Record ID 6478215, Apr. 2019, 2 pages.
Derma E, "Skin Brighten", Retrieved online <https://dermae.com/products/skin-brighten>, 10 pages, 2022.
Database GNPD [Online], Mintel, Dr. Dennis Gross Skincare, USA, "Wrinkle Recovery Overnight Serum", Record ID 3700421, published Jan. 2016, 7 pages.
Eminence," Rosehip Triple C+E Firming Oil", Retrieved online <https://eminenceorganics.com/US/product/osehip-triple-ce-firming-oil>, 8 p. 2022.
Database GNPD [Online], Mintel, FarmHouse Fresh, USA, "Three Milk Ageless Moisturizer", Record ID 3876115, published Mar. 2016, 2 pages.
Database GNPD [Online], Mintel, StriVectin, USA, "Multi-Action Active Infusion Youth Serum ", Record ID 4705593, published Mar. 2017, 5 pages.
Database GNPD [Online], Mintel, Sunday Riley Modem Skincare, USA, "U.F.O. Ultra-Clarifying Acne Treatment Face Oil", Record ID 4435431, published Nov. 2016, 2 pages.

* cited by examiner

*Primary Examiner* — Qiuwen Mi
(74) *Attorney, Agent, or Firm* — Laetitia Leproust; Robert Klemz (57) ABSTRACT

Cosmetic compositions comprising high amount of *Silybum marianum* Extract, relatively high amounts of skin active ingredients chosen from salicylic acid, ascorbic acid, a cinnamic acid derivative, or a mixture thereof; c) one or more surfactants; d) from about 3 to about 15 wt. % of Propylene Glycol; e) from about 5 to about 18 wt. % of Dipropylene Glycol; and f) water; and wherein the composition has a pH not higher than about 5.

8 Claims, 2 Drawing Sheets

SERUMS FOR REDUCING LIPID PEROXIDATION

FIELD OF THE INVENTION

The present disclosure relates to cosmetic compositions comprising *Silybum marianum* Extract, relatively high amounts of skin active ingredients, glycols and water; and methods for treating skin using the cosmetic compositions.

BACKGROUND OF THE INVENTION

UV exposure and environmental pollution can accelerate skin aging by producing free radicals in skin. Antioxidants, including Vitamin C, and other actives protect cells from the damage of oxidative stress by scavenging free radicals and inhibiting oxidation reactions. The topical application of antioxidants and other skin actives is broadly employed in skin care products to prevent skin aging. There are challenges with providing compositions that include suitably high amounts of actives, including antioxidants, in a system that can stably maintain solubility of the actives over time and at ambient temperatures. The commercial compositions that are formulated with high amounts of actives suffer from short shelf lives or their effectiveness is diminished due to instability and ultimate precipitation of actives. Thus, many commercial compositions include amounts of actives that may be insufficient for addressing the risks faced by a consumer. There remains a need for systems for formulating protective compositions that offer meaningful levels of protective actives in a stable formulation.

SUMMARY OF THE DISCLOSURE

The present disclosure relates to cosmetic compositions that are unique in comparison to conventional cosmetic compositions because they contain and deliver a high concentration of *Silybum marianum* Extract, a high concentration of skin active ingredients, such as ascorbic acid and salicylic acid in a water/glycols system. High concentration of *Silybum marianum* Extract, ascorbic acid, and salicylic acid are very difficult to stabilize, each for different reasons, and therefore pose unique formulation challenges. While not wishing to be bound by any particular theory, the inventors believe that *Silybum marianum* Extract, in combination with a specific blend of glycols in a water system, as well as a ratio, contribute to the solubility, stability and therefore to the effectiveness of the compositions. The cosmetic compositions typically include:
  a) about 0.1 to about 1.8 wt. % of *Silybum marianum* Extract;
  b) one or more skin active chosen from salicylic acid, ascorbic acid, a cinnamic acid derivative, or a mixture thereof;
  c) one or more surfactants;
  d) from about 3 to about 15 wt. % of Propylene Glycol;
  e) from about 8 to about 18 wt. % of Dipropylene Glycol; and
  f) water; and
    wherein the composition has a pH not higher than about 5;
    wherein all percentages by weight are based on the total weight of the cosmetic composition.
In an embodiment, the *Silybum marianum* Extract is present in amounts sufficient to prevent lipoperoxidation activity on skin.

The cosmetic compositions may be in the form of an aqueous serum, gel, essence, and light lotion. It can be useful for the pH to be acidic (less than 7) to help maximize the efficacy of ascorbic acid.

In some embodiments, the weight ratio of the glycol blend of Propylene glycol to Dipropylene Gycol is about 1:6 to about 1:1.

In one or more embodiments, the total amount of skin care actives present in the composition is from about 0.1 to about 20 wt. % based on the total weight of the cosmetic composition.

In one or more embodiments, the compositions may comprise a glycol other than Propylene Glycol or Dipropylene Glycol and chosen from ethylene glycol, butylene glycol, hexylene glycol, pentylene glycol, 1,3-propanediol, diethylene glycol, dipropylene glycol, propylene glycol (=1,2-Propanediol), caprylyl glycol, glycerin, and a mixture thereof.

In some embodiments, Propylene Gycol is present from about 5 to about 12 wt. %, or from about 5 to about 10 wt. %, based on the total weight of the cosmetic composition. In one or more embodiments, Dipropylene Glycol is present from about 8 to about 15 wt. %, or from about 10 to about 15 wt. %, based on the total weight of the cosmetic composition.

In one or more embodiments, the one or more surfactants is present from about 1 to about 10 wt. % based on the total weight of the cosmetic composition. In some embodiments, the one or more surfactants include alkoxylated fatty alcohols.

In one or more embodiments, the compositions demonstrate solubility and stability of the *Silybum marianum* Extract at temperatures in the range from about 5° C. to about 45° C. and at a pH that is not higher than about 5.

In one or more embodiments, the water is present from about 35 to about 90 wt. %, or from about 35 to about 80 wt. %, or from about 35 to about 70 wt. %, or from about 35 to about 60 wt. %, or from about 35 to about 50 wt. %, based on the total weight of the cosmetic composition.

In some embodiments, the cinnamic acid derivative is ferulic acid. In some embodiments, the one or more skin active agent comprises salicylic acid and ascorbic acid.

Another aspect of the instant disclosure can include:
  a) about 0.1 to about 1.8 wt. % of *Silybum marianum* Extract;
  b) about 0.1 to about 2 wt. % of salicylic acid;
  c) about 2 to about 20 wt. % of ascorbic acid;
  d) one or more surfactants including alkoxylated fatty alcohols;
  e) from about 3 to about 10 wt. % of Propylene Glycol;
  f) from about 10 to about 18 wt. % of Dipropylene Glycol; and
  g) water; and
    wherein the composition has a pH not higher than about 5; and
    wherein all percentages by weight are based on the total weight of the cosmetic composition.

In an embodiment, the *Silybum marianum* Extract is present in amounts sufficient to prevent or minimize lipoperoxidation activity on skin.

In another exemplary embodiment, the present invention is related to a method for treating skin comprising applying the cosmetic composition of instant disclosure to the skin.

The cosmetic compositions are useful for treating skin, for example, the skin of the face and neck of a human. Thus, the instant disclosure relates to methods of treating the skin comprising applying the cosmetic composition of the instant disclosure to the skin. The cosmetic compositions are additionally useful in methods for treating skin dryness, repairing skin damage due to photoaging, and diminishing the appearance of wrinkles, dark spots, and uneven skin texture. The aforementioned methods may be non-therapeutic.

The instant disclosure also relates to methods of preventing or minimizing lipoperoxidation activity on skin, the method comprising applying the cosmetic compositions of the instant disclosure to the skin.

These and other aspects of the invention are set out in the appended claims and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

BRIEF DESCRIPTION OF THE DRAWINGS

Implementations of the present technology will now be described, by way of example only, with reference to the attached figures, wherein.

It should be understood that the various aspects are not limited to the arrangements and instrumentality shown in the drawings.

DETAILED DESCRIPTION OF THE DISCLOSURE

The present disclosure relates to cosmetic compositions that are unique in comparison to conventional cosmetic compositions because they contain and deliver a high concentration of *Silybum marianum* Extract, a high concentration of skin active ingredients, such as ascorbic acid and salicylic acid in a water/glycol system. High concentration of *Silybum marianum* Extract, ascorbic acid, and salicylic acid are very difficult to stabilize, each for different reasons, and therefore pose unique formulations challenges. The cosmetic compositions typically include:
  a) about 0.1 to about 1.8 wt. % of *Silybum marianum* Extract;
  b) one or more skin active chosen from salicylic acid, ascorbic acid, a cinnamic acid derivative, or a mixture thereof;
  c) one or more surfactants;
  d) from about 3 to about 15 wt. % of Propylene Glycol;
  e) from about 8 to about 18 wt. % of Dipropylene Glycol; and
  f) water; and
  wherein the composition has a pH not higher than about 5; and
  wherein all percentages by weight are based on the total weight of the cosmetic composition.

In an embodiment, the *Silybum marianum* Extract is present in amounts sufficient to prevent or minimize lipoperoxidation activity on skin.

The term "lipoperoxidation activity" used herein is understood to refer to the oxidation of lipids which is typically catalyzed by free radicals.

The term "stability" used herein is understood to describe a cosmetic composition which does not change significantly in appearance following standardized storage protocols, which may include storage of formulations at various temperatures from about 4 degrees Celsius up to about 45 degrees Celsius for prolonged periods greater than 2 months. In particular, "stability" within the present disclosure relates to the visual appearance (either aided by using a microscope or unaided) of crystals or solid particles that precipitate out of the formulation during periods of prolonged, temperature-controlled storage. Keeping the formula visually consistent and intact and no changes macroscopically in clarity or microscope image.

The term "solubility" used herein is understood to explain the ability to dissolve into a homogeneous solution with no change in visual or microscope cloudiness or particulates.

*Silybum marianum* Extract

*Silybum marianum* extract (containing Silymarin) is extracted from the fruit of the milk thistle plant (*Silybum marianum*) and contains several flavonoids and flavonolignans including the principal components silybin, which is predominant (i.e. active), silydianin, and silychristin. Silymarin is known to have anti-inflammatory, hepatoprotective and anticarcinogenic effects.

The cosmetic compositions include *Silybum marianum* extract. For example, the cosmetic composition may include an amount of *Silybum marianum* extract ranging from about 0.1 wt. % to about 1.8 wt. %, about 0.2 wt. % to about 1.6 wt. %, about 0.3 wt. % to about 1.4 wt. %, about 0.4 wt. % to about 1.2 wt. %, about 0.5 wt. % to about 1 wt. % including ranges and sub-ranges there between, based on the total weight of the composition.

Additionally, *Silybum marianum* extract is present from about 0.1, 0.15, 0.2, 0.25, 0.3, 0.35, 0.4, 0.45, 0.5 0.55, 0.6, 0.65, 0.7, 0.75, 0.8, 0.85, 0.9 to about 0.9, 0.95, 1.0, 1.1, 1.15, 1.2, 1.25, 1.3, 1.35, 1.4, 1.45, 1.5, 1.55, 1.6, 1.65, 1.7, 1.75, or 1.8 wt. % based on the total weight of the cosmetic composition.

Skin Actives

In accordance with the instant disclosure, embodiments of the composition include one or more skin actives chosen from salicylic acid, ascorbic acid, a cinnamic acid derivative, or a mixture thereof. In some specific embodiments, the composition comprises each of ascorbic acid, a cinnamic acid derivative comprising ferulic acid.

The cosmetic compositions include salicylic acid. For examples, the cosmetic compositions may include an amount of salicylic acid ranging from about 0.1 wt. % to about 2.0 wt. %, about 0.2 wt. % to about 1.8 wt. %, about 0.3 wt. % to about 1.7 wt. %, about 0.4 wt. % to about 1.6 wt. %, about 0.5 wt. % to about 1.5 wt. % including ranges and sub-ranges there between, based on the total weight of the composition.

In some embodiments, the compositions include ascorbic acid. For examples, the cosmetic compositions may include an amount of ascorbic acid from about 1.0 wt. % to 30 wt. %, 2.5 wt. % to 25 wt. %, 3.5 wt. % to 20 wt. %, 4.5 wt. % to 20 wt. %, 5 wt. % to 18 wt. %, 6 wt. % to 18 wt. %, 7 wt. % to 15 wt. %, or 8 wt. % to 15 wt. % including ranges and sub-ranges there between, based on the total weight of the composition. Likewise, in some embodiments, the cosmetic composition may include an amount of ascorbic acid that is about 20 wt. %, about 19 wt. %, about 18 wt. %, about 17 wt. %, about 16 wt. %, about 15 wt. %, about 14 wt. %, about 13 wt. %, about 12 wt. %, about 11 wt. %, about 10 wt. %, about 9 wt. %, about 8 wt. %, about 7 wt. %, about 6 wt. %, about 5 wt. %, about 4 wt. %, about 3 wt. %, about 2 wt. % or about 1 wt. %, based on the total weight of the composition. In one embodiment, the amount of ascorbic acid may be from about 10 to about 15 wt. %, or from about 12 to about 15 wt. % of the total weight of the cosmetic composition.

The ascorbic acid may be L-ascorbic acid, a mixture of L-ascorbic acid and R-ascorbic acid, and/or a racemic mixture. In one embodiment, the ascorbic acid comprises only L-ascorbic acid, essentially only L-ascorbic acid, and/or at least 75 wt. %, at least 85 wt. %, at least 90 wt. %, at least 95 wt. %, or at least 99 wt. % of L-ascorbic acid, based on the total weight of ascorbic acid.

Ascorbic acid is also known as Vitamin C. Ascorbic acid may be provided by the addition of any reducing analog of ascorbic acid, such as D-isoascorbic acid or by the addition of other small reducing compounds such as, but not limited to, glutathione, L-cysteamine, and the like. Such forms would be expected to provide an equivalent composition to that claimed and are within the scope of the invention.

In some embodiments, the one or combination of skin actives comprises a cinnamic acid derivative. A cinnamic acid or derivative thereof may be selected from the group consisting of ferulic acid, p-coumaric acid, caffeic acid, sinapinic acid, chlorogenic acids, caftaric acid, chicoric acid, coutaric acid, rosmarinic acid, derivatives thereof, and combinations thereof. Equivalent derivatives thereof include those cinnamic acid derivatives having substitutions on the hydroxyl groups of the aromatic ring such as short chain aliphatic groups (one to six carbon atoms) or long chain aliphatic groups (seven to twenty-four carbon atoms) to form an ether, or such aliphatic groups substituted with alkyl, alkoxy, hydroxyl, amino, or amido, for example, to form a substituted ether. Equivalent derivatives thereof further include those cinnamic acid derivatives having modifications of the methoxy group(s) of the aromatic ring to short chain aliphatic groups (two to six carbon atoms) or to long chain aliphatic groups (seven to twenty-four carbon atoms) to form a longer chain ether, or such aliphatic groups substituted with alkyl, alkoxy, hydroxyl, amino, or amido, for example, to form a substituted long chain ether. The 3-carboxy group of a cinnamic acid derivative may also be converted to esters or amides having aliphatic groups of up to 24 carbons or an aromatic group, for example. Cis and trans isomers of the cinnamic acid derivatives are included herein since the cis isomer is readily converted to the trans isomer. Salts of the cinnamic acid derivatives are included herein. In one embodiment, the cinnamic acid derivative is a triethanolamine salt. Caffeic acid, also known as 3-(3,4-dihydroxyphenyl)-2-propenoic acid, is found in many fruits, vegetables, seasonings and beverages consumed by humans. Caffeic acid is present in such goods in conjugated forms such as chlorogenic acid. Para-coumaric acid, also known as 3-(4-hydroxyphenyl)-2-propenoic acid or p-hydroxycinnamic acid, is found in various plants, including lignin forming plants. Trans-ferulic acid, also known as 3-(4-hydroxy-3-methoxyp-henyl)-2-propenoic acid or 4-hydroxy-3-methoxycinnamic acid, is also widely distributed in small amounts in plants. Sinapinic acid, also known as 3,5-dimethoxy4-hydroxycinnamic acid, is from black mustard seeds. Caffeic acid, para-coumaric acid, trans-ferulic acid and sinapinic acid are commercially available from Sigma-Aldrich.

In some embodiments, additional actives can also include at least one hydroxy acid selected from alpha, beta or polyhydroxy acids. Thus, in various embodiments, a hydroxy acid may be selected from the group consisting of lactic acid, glycolic acid, salicylic acid, malic acid, tartaric acid, citric acid, mandelic acid, lactobionic acid, gluconolactone, galactose, and combinations thereof.

Generally, each of the skin actives can be present in the composition in an amount from about 0.1% to about 30%, and in some embodiments, from about 0.5% to about 30%, and in some embodiments, from about 0.5% to about 15%, and in some embodiments, from about 0.1% to about 1%, and in some embodiments, from about 1% to about 2%, or any suitable combination, sub-combination, range, or sub-range thereof, by weight, based on the weight of the composition.

Ascorbic acid and its derivatives may be present in the composition in an amount from about 1% to about 30%, and in some embodiments, from about 5% to about 25%, and in some embodiments, from about 10% to about 20%, and in some embodiments, from about 10% to about 15%, or any suitable combination, sub-combination, range, or sub-range thereof, by weight, based on the weight of the composition.

Cinnamic acid derivatives, including, but not limited to ferulic acid, and triethanolamine salts may be present in the compositions in an amount from about 0.1% to about 1%, and in some embodiments, from about 0.1% to about 0.5%, and in some embodiments, from about 0.5% to about 1.0%, or any suitable combination, sub-combination, range, or sub-range thereof, by weight, based on the weight of the composition.

Thus, in various embodiments, each of the skin actives may be present in a composition according to the disclosure in an amount of about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19, 20, 21, 22, 23, 24, 25, 26, 27, 28 to about 30 percent by weight, including increments and ranges there between.

In accordance with some embodiments, the composition comprises more than one skin care active and the combination thereof is present in the composition at a total concentration, of from about 1 to about 30 wt. %. In some embodiments, the total amount of skin care actives present in the composition is in a range from about 10 to about 30 wt. %, or from about 12 to about 25 wt. %, or from about 14 to about 20 wt. %, or from 15 to about 18 wt. %, based on the weight of the composition.

In various embodiment, the composition comprises a skin care active comprising salicylic acid and ascorbic acid in a total amount of from about 10 to about 30 wt. %, or from about 12 to about 25 wt. %, or from about 14 to about 20 wt. %, or from 15 to about 18 wt. %, based on the weight of the composition.

Thus, in various embodiments, the total amount of the skin actives may be present in a composition according to the disclosure in an amount of from about 1.0, 2, 3, 4, 5, 6, 7, 8, 9, 10, 11, 12, 13, 14, 15, 16, 17, 18, 19, 20, 21, 22, 23, 24, 25, 26, 27, 28 to about 30 wt. %, including increments and ranges there between.

Surfactants

In accordance with the disclosure, embodiments of the composition comprise one or more surfactants. In some embodiments, the one or more surfactants is present from about 1 to about 10 wt. % based on the total weight of the cosmetic composition.

The one surfactant or more surfactants may be a nonionic, cationic, anionic, or a zwitterionic surfactant. The at least one surfactant may be selected from alkoxylated fatty alcohols. Suitable examples of alkoxylated fatty alcohols include laureth-3, laureth-7, laureth-9, laureth-12, laureth-23, ceteth-10, ceteth-33, steareth-10, steareth-2, steareth-20, steareth-100, beheneth-5, beheneth-5, beheneth-10, oleth-10, Pareth alcohols, trideceth-10, trideceth-12, C12-13 pareth-3, C12-13 pareth-23, C1 1-15 pareth-7, PPG-5 ceteth-20, PEG-55 Propylene Glycol Oleate, glycereth-26 (PEG-26 Glyceryl Ether), PEG 120 methyl glucose dioleate, PEG 120 methyl glucose trioleate, PEG 150 pentaerythrityl tetrastearate, and mixtures thereof. The one or more surfactants may be present in the composition in a range from about 1 to about 10% wt. % on the total weight of the cosmetic composition.

In some particular embodiments the one surfactant comprises laureth-23.

In various embodiments, the at least one surfactant may be present from about 1% to about 5% on the total weight of the cosmetic composition, and in some embodiments, from about 1% to about 4%, and in some embodiments, from about 3% to about 6%, and in some embodiments, from about 3% to about 4.5%, or any suitable combination, sub-combination, range, or sub-range thereof by weight, based on the weight of the composition. In some embodiments, laureth-23 may be present from about 1 to about 10 wt. % by weight of the composition, and in some embodiments, from about 3% to about 4.5%, or any suitable combination, sub-combination, range, or sub-range thereof by weight, based on the weight of the composition. In some embodiments, alkoxylated fatty alcohols may be present from about 1% to about 10% by weight of the composition, and in some embodiments, from about 1% to about 2%, or any suitable combination, sub-combination, range, or sub-range thereof by weight, based on the weight of the composition. In some embodiments, the composition comprises more than one surfactant. One of ordinary skill in the art, however, will appreciate that other ranges are within the scope of the invention.

Thus, in various embodiments, each of the one or more surfactants is present in a composition according to the disclosure from about 1, 2, 3, 4, 5, 6, 7, 8, 9, to about 10 percent, by weight, including increments and ranges therein and there between.

Glycols

In accordance with the disclosure, the composition includes propylene glycol and dipropylene glycol.

In various embodiments, the compositions may further comprise a glycol other than Propylene Glycol or Dipropylene Glycol and chosen from ethylene glycol, butylene glycol, hexylene glycol, pentylene glycol, 1,3-propanediol, diethylene glycol, dipropylene glycol, propylene glycol (=1, 2-Propanediol), caprylyl glycol, glycerin, and a mixture thereof.

In various embodiments, propylene glycol is present in the composition in a range from at least about 3% to about 15%, such as in an amount from at least about 3.2% to about 14.5%, 3.4% to about 14%, to about 3.6% to about 13%, to about 3.8% to about 13.5%, to about 4% to about 13%, to about 4% to about 12%, to about 4.5% to about 11% and in some embodiments, from about 4.5% to about 10%, or any suitable combination, sub-combination, range, or sub-range thereof by weight, based on the weight of the composition.

In various embodiments, the dipropylene glycol is present in the composition in a range of from about 8% to 18%, or from at least about 8.5% to about 17.5%, or at least about 9% to about 17%, or at least about 9.5% to about 16.5%, or at least about 10% to about 15%, and in some embodiments, from about 10% to about 12%, or any suitable combination, sub-combination, range, or sub-range thereof by weight, based on the weight of the composition.

In various embodiments, the glycol or combination of glycols may comprise a combination of propylene glycol and dipropylene glycol present in a ratio in a range from about 1:6 to about 1:1 propylene glycol to dipropylene glycol. In some embodiments, the ratio of propylene glycol to dipropylene glycol is about 1:6, and in some embodiments it is about 1:3, and in some embodiments, it is about 1:1. In some embodiments, the ratio of propylene glycol and dipropylene glycol is in a range from about 1:6 to about 1:1, from about 1:4 to about 1:1, from about 1:3 to about 1:1, from about 1:2 to about 1:1, from about 1:1.5 to about 1:1, or any suitable combination, sub-combination, range, or sub-range thereof.

The total amount of the combination of glycols present in the composition is in a range from at least about 25% to less than about 20%, and in some embodiments from at least about 20% to less than about 15%, all amounts and ratios based on the weight of the composition. Propylene glycol may be present in the combination within the composition in an amount from at least about 3% to about 15%, and in some embodiments, from about 6% to about 12%, and in some embodiments, from about 3% to about 10%, and in some embodiments, from about 8% to about 10%, or any suitable combination, sub-combination, range, or sub-range thereof by weight, based on the weight of the composition. Dipropylene glycol may be present in the combination within the composition in an amount from at least about 8% to about 18%, and in some embodiments, from about 9% to about 17%, and in some embodiments, from about 110% to about 16.5%, and in some embodiments, from about 10% to about 14%, or any suitable combination, sub-combination, range, or sub-range thereof by weight, based on the weight of the composition.

Thus, in various embodiments, each of the glycols is present in a composition according to the disclosure from about 3, 4, 5, 6, 7, 8, 9, 10, 11, 12, 13, 14, 15, 16, 17, to about 18 percent, by weight, including increments and ranges therein and there between.

Water

In accordance with the various embodiments, water is present in the compositions in a range from about 35% to about 90%, and in some embodiments, from about 35% to about 70%, and in some embodiments, from about 35% to about 65%, and in some embodiments, from about 35% to about 60%, and in some embodiments, about 68% or any suitable combination, sub-combination, range, or sub-range thereof by weight, based on the weight of the composition. One of ordinary skill in the art, however, will appreciate that other ranges are within the scope of the invention. Thus, water is present, by weight, based on the total weight of the composition, from about 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, to about 90 percent, by weight, including increments and ranges therein and there between. One of ordinary skill in the art, however, will appreciate that other ranges are within the scope of the invention.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition is not limited but is generally between about 2.0 and about 5.0, and in some embodiments, is one of between about 3 and about 4.5. The pH can be adjusted to the desired value by addition of a base (organic or inorganic) to the composition, for example, sodium citrate, ammonia or a primary, secondary or tertiary (poly) amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Optional Additives

The compositions may also comprise at least one additive used in the cosmetics field which does not affect the properties of the compositions according to the invention, such as fragrances, preservatives, anti-microbials, coloring materials, essential oils, citric acid, sodium citrate, sodium chloride, pH-adjusting agents, chelating, and combinations thereof. In some particular embodiments, the compositions may comprise at least one additive selected from: preservatives/anti-microbials, for example, phenoxyethanol, potassium sorbate, and caprylyl glycol; actives, for example, hydroxyacetophenone, and vitamins, and UV agents such as terephthalylidene dicamphor sulfonic acid; coloring materials; essential oils; citric acid, sodium citrate, sodium chloride; neutralizing, chelating or pH-adjusting agents (for example, triethylamine (TEA), trisodium ethylenediamine disuccinate, and sodium hydroxide), and combinations thereof.

Preservatives having antibacterial activity are optionally present in the compositions of the present invention. Any preservative commonly used in cosmetic formulations is an acceptable preservative for the compositions herein, such as phenoxyethanol, members from the paraben family such as the methyl, ethyl, propyl, butyl or isobutyl parabens, 4-hydroxy benzoic acid, benzoic acid, sorbic acid, dehydroacetic acid, triclosan, benzyl alcohol, chlorophenesin, or salicylic acid, for example. Phenoxyethanol is commercially available from Sigma-Aldrich. At more concentrated amounts of solvent, members from the paraben family may be used as a preservative.

Although the optional additives are given as examples, it will be appreciated that other optional components compatible with cosmetic applications known in the art may be used that are suitable.

In some particular embodiments, the composition may include optional additives selected chosen from phenoxyethanol, terephthalylidene dicamphor sulfonic acid, trisodium ethylenediamine disuccinate, sodium citrate, sodium chloride, hydroxyacetophenone sodium benzoate, potassium sorbate, citric acid, caprylyl glycol, and trisodium ethylenediamine disuccinate, and combinations thereof. In some embodiments, phenoxyethanol is present in the composition in a range from about 0.5% to about 2%, and in some embodiments in a range from about 1% to about 2%.

In accordance with the various embodiments, the amount of one or more actives and additives, alone or in combination, when present in the composition according to the disclosure can be present in a range from about 0.001% to about 20%, and in some embodiments, from about 0.05% to about 0.01%, and in some embodiments, from about 0.01% to about 0.1%, and in some embodiments, from about 0.15% to about 5%, and in some embodiments, from about 0.40% to about 4%, and in some embodiments, from about 0.5% to about 2.5%, and in some embodiments, from about 0.1% to about 0.5% and in some embodiments, from about 1% to about 2%, or any suitable combination, sub-combination, range, or sub-range thereof by weight, based on the total weight of the composition. One of ordinary skill in the art, however, will appreciate that other ranges are within the scope of the invention.

Thus, any one or a combination of actives and additives may be present, each one or the combination present from about 0.001, 0.005, 0.01, 0.02, 0.03, 0.04, 0.05, 0.06, 0.07, 0.08, 0.09, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 percent, by weight, including increments and ranges therein and there between.

EXAMPLES

Implementation of the present disclosure is provided by way of the following examples. The following examples serve to elucidate aspects of the technology without being limiting in nature.

Example 1

Inventive Compositions

TABLE 1

| | | INCI US | Inv. Ex. 1 |
|---|---|---|---|
| (a) | | SILIBUM MARIANUM EXTRACT (SILYMARIN) | 0.64 |
| (b) | | SALICYLIC ACID | 0.5 |
| | | ASCORBIC ACID | 15 |
| | | FERULIC ACID | 0.5 |
| (c) | Surfactant | LAURETH-23 | 3 |
| (d) | Glycols | DIPROPYLENE GLYCOL | 10 |
| (e) | Glycols | PROPYLENE GLYCOL | 10 |
| (f) | Water | WATER | Q.S.100 |

Example 2

Physical Stability

The Inventive Example 1 was tested for a 12-weeks physical stability at 5° C., 25° C., 37° C., 45° C., and F/T (i.e., Freeze/Thaw). The Inventive Example 1 was dispensed in four different glass jars.

It was observed that at initial time T0, the 4 glass jars containing the Inventive Example 1 were macroscopically and microscopically clear.

After four weeks, it was observed that the 4 glass jars containing the Inventive Example 1 were still macroscopically and microscopically clear. The samples being exposed at 37° C. and 45° C. were a little bit darker in color, but they were clear.

After eight weeks, it was observed that the 4 glass jars containing the Inventive Example 1 were still macroscopically and microscopically clear. The samples being exposed at 37° C. and 45° C. exhibited a darker color than at four weeks, but both samples were still clear (both macroscopically and microscopically).

After 12 weeks, it was observed that the 4 glass jars containing the Inventive Example 1 were still macroscopically and microscopically clear. The samples being exposed at 37° C. and 45° C. exhibited a very dark color compare to the eight-week study, but both samples were still clear (both macroscopically and microscopically).

Conclusion:

After the 12-week stability, it appeared that all the samples were macroscopically and microscopically clear from the initial time through the 12 weeks indicating good solubility throughout 12-week stability at 5° C., 25° C., 37° C., 45° C., and F/T.

One of the big challenges of using *Silybum marianum* Extract in a water/glycols solvent environment was to be able to have the *Silybum marianum* Extract solubilized and then stay stable. The ratio of the solvent system was carefully studied as it was not obvious to be able to solubilized *Silybum marianum* Extract in such solvent system.

Example 3

Solubility/Stability

Hansen space was done to examine what solvents could be used based on the principle "like dissolves like" the solvent closest to *Silybum marianum* Extract in the 3D Space (representing the dispersion forces (D), polarity (P) and hydrogen bonds showed the closest solvents that can be used were Dipropylene Glycol, Proprylene Glycol, and Alcohol. The solvents were evaluated at different percentages.

Results
  20% Glycol blend didn't always result in clear formulas, even in cases with similar water levels between 44-46%.
  The clear stability of the *Silybum marianum* Extract in ascorbic acid was dependent on the specific amount of 20% Glycols that was used.
  In the case of other systems with 13%-20% Glycols (Butylene, Dipropylene) with varying levels of glycols, a separation was observed.

Ingredient Metering

Stability was assessed by an experiment called "metering", which entails placing samples at elevated temperatures (45 C) for up to 3 months and testing the samples at set 4 week intervals using Liquid Chromatography-UV (LC-UV) to determine concentration of active ingredients.

The levels of Ascorbic Acid, Ferulic Acid, Salicylic Acid, and *Silybum marianum* Extract (Active Silybin) were metered.

Silybin is an antioxidant which is a main active component in *Silybum marianum* Extract. Higher concentrations of silybin are expected to have lower aqueous solubility, but this can be improved at higher pH's. However, the inventive examples exist in an acidic environment, which makes it even more challenging to solubilize the silybin.

The data show that the cosmetic compositions according to the instant disclosure, which included high amounts of *Silybum marianum* Extract, salicylic acid and ascorbic acid were surprisingly stable in the water/glycols solvent system at low pH.

TABLE 3

Solubilization of Silybum Marianum Extract in Inventive Examples

| Glycol | Inv. Ex. 1 % | Inv. Ex. 2 % | Inv. Ex. 3 % |
| --- | --- | --- | --- |
| Silybum Marianum Extract | 0.64 | 0.64 | 0.64 |
| Pentylene Glycol | 0 | 0.0 | 0.0 |
| Propylene Glycol | 10.00 | 5.0 | 8.0 |
| Dipropylene Glycol | 10.00 | 15.0 | 12.0 |
| Butylene Glycol | 0.00 | 0.00 | 0.00 |
| Glycerin | 0.00 | 0.00 | 0.00 |
| Total Glycols | 20.0 | 20.0 | 20.0 |
| Initial Results | Clear | Clear | Clear |
| Results after 2 weeks | Clear | Clear | Clear |

In Table 3 above, it was shown that the blend of glycols was essential to the physical stability of the inventive formula. Inventive Examples stayed clear in all conditions for 12 weeks accelerated stability, including 5° C.

Inventive Ex. 1, 2 and 3 showed how the ratio of Propylene Glycol and Dipropylene glycol was essential.

The results show that a combination of glycols selected from propylene glycol and dipropylene glycol provide a composition that is stable in the presence of a high amount of actives in a range from 0.1% to 30% that include ascorbic acid at or near its solubility limit in water.

TABLE 2

Stability of ingredients in inventive formula

| Inventive Ex. 1 | Theoretical | T0 M* | T1M TA** | T1M 45° C | T2M TA | T2M 45° C |
| --- | --- | --- | --- | --- | --- | --- |
| Ascorbic Acid | 15% | 15.2% | 15.04% | 14.72% | 15.60% | 14.00% |
| Ferulic Acid | 0.50% | 0.46% | 0.48% | 0.43% | 0.50% | 0.39% |
| Salicylic Acid | 0.50% | N/A | 0.50% | 0.49% | 0.49% | 0.47% |
| Silybum Marianum Extract (Active Silybin) | 0.21% | N/A | 0.24% | 0.22% | 0.20% | 0.18% |

*Month
**Temperature Ambient

TABLE 4

Solubilization of Silybum Marianum Extract in Comparative Examples.

| Glycol | Comp. Ex. 2 % | Comp. Ex. 3 % | Comp. Ex. 4 % | Comp. Ex. 5 % | Comp. Ex. 6 % | Comp. Ex. 7 % | Comp. Ex. 8 % |
|---|---|---|---|---|---|---|---|
| Silybum Marianum Extract | 0.64 | 0.64 | 0.64 | 0.64 | 0.64 | 0.64 | 0.64 |
| Pentylene Glycol | 5 | 0 | 0.0 | 0.0 | 0.00 | 0.0 | 0.0 |
| Propylene Glycol | 7.83 | 0 | 12 | 20.0 | 15.00 | 12.0 | 0.0 |
| Dipropylene Glycol | 0 | 15 | 5 | 0.00 | 5.00 | 8.0 | 0.0 |
| Butylene Glycol | 0 | 5 | 0 | 0.00 | 0.00 | 0.00 | 0.0 |
| Glycerin | 0.00 | 0.00 | 0.00 | 0.00 | 0.00 | 0.00 | 20.0 |
| Total Glycols | 12.83 | 20.0 | 17.0 | 20.0 | 20.0 | 20.0 | 20.0 |
| Initial Results | Unstable | Unstable | Clear | Clear | Clear | Clear | Clear |
| Results After 2 weeks | Unstable | Unstable | Unstable | Unstable | Unstable | Unstable | Unstable |

In Table 4 above, all the Comp. Ex. used different ratios of glycols as well as different types of glycols. It was then observed that Silybin was very instable in those formulas (precipitate formed at 5° C. after about 1-2 weeks). Failure was shown by the visible separation that was observed.

Even with a total glycol content of 20%, it was observed that the comparative examples could also be clear but were not stable.

In conclusion, as shown in Table 3, with the level of *Silybum marianum* Extract maintained at 0.64%, it was unexpectedly found that a specific ratio between the propylene glycol and the dipropylene glycol was necessary to maintain the solubility and the stability of the *Silybum marianum* Extract (Active Silybin) in a water acidic environment.

Example 4

Evaluation

An ex-vivo sebum photo peroxidation test was done to evaluate the antioxidant effectiveness of the inventive formula. In this test, sebum treated with the inventive formula was compared to untreated sebum (Control) to assess its ability to reduce UVA-induced sebum peroxidation.

Results

The results of the effectiveness of the inventive formula compared to the sebum alone are summarized in the following tables:

Test Conditions

Figure 1:
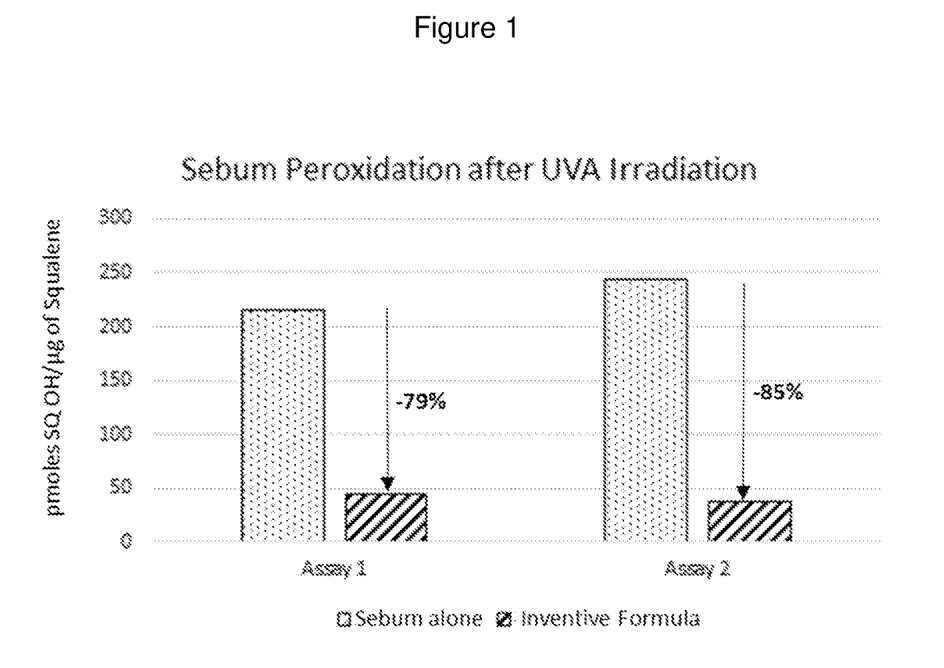
FIG. 1 graphically shows % of sebum peroxidation after UVA irradiation.

A sebum layer was taken from a volunteer's forehead on 2 inert mediums. Around 5 mg/cm$^2$ of the active formula to be tested was applied to the first sample, with nothing being applied to the second sample (untreated sebum control). The samples were exposed to UVA at 5 joules/cm$^2$. Sebum photo-oxidation lead to the formation of squalene peroxides, and variation in peroxidation allows us to compare the effectiveness of the active formula versus the sebum alone. See FIG. 1.

Conclusion

It was observed that the inventive formula was effective compared to the untreated sebum, which was seen by inhibition of sebum peroxidation around 82% in the test conditions.

Example 5

MDA Assay for Peroxidation

Studies have shown that *Silybum marianum* Extract plays a protective role against the oxidative damage induced by environmental contaminants like benzo(a)pyrene in erythrocyte haemolysates. Description of these studies can be found in K. Pandima Devi et al. "Silymarin Protection against Major Reactive Oxygen Species Released by Environmental Toxins: Exogenous H2O2 Exposure in Erythrocytes" *Nordic Pharmacological Society. Basic & Clinical Pharmacology & Toxicology*, 100, 414-419, 2007.

| | Squalene Peroxide (SQOOH) in pmoles/µg of Squalene (SQ) | | |
|---|---|---|---|
| UVA exposure 5 joules/cm$^2$ | Control | Inventive Formula 1 | inhibition |
| ASSAY 1 | 216 ± 5 | 44 ± 2 | 82 ± 3% |
| ASSAY 2 | 244 ± 4 | 37 ± 1 | |

Protection to photo peroxidation provided by inventive formula was effective, with inhibition at around 82% compared to the untreated sebum. The level of effectiveness can be explained by the combined effect of antioxidant protection (Ascorbic Acid 15%+*Silybum marianum* Extract 0.64%+Ferulic Acid 0.5%).

Lipid-Peroxidation Inhibition Testing:

Applicants studied the effect of Silymarin in the formula and compared the lipoperoxidation results to well-known Tocopherol (i.e. Vitamin E) to examine that the percentage picked was showing an effect in the formulation. The experiments consisted to strip skin's sebum where inventive formula was applied to confirm the reduction of lipid peroxidation. The reduction of lipid peroxidation is not common for many anti-oxidants and it was shown that the silymarin level at 0.5% was well dosed compared to the effect of well-known Tocopherol at 0.5%. See FIG. 2.

Figure 2:
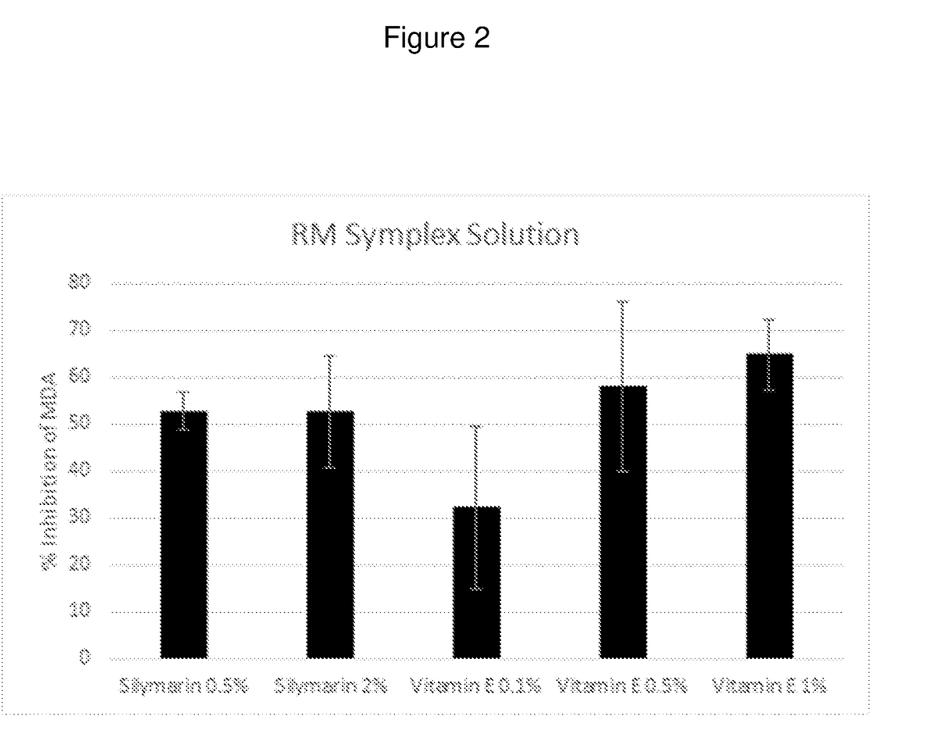
FIG. 2 graphically shows % inhibition of the raw material to be able to prevent the formation of malondialdehyde after skin samples are exposed to UV light.

Indeed, it was observed in FIG. 2 that the presence of Silymarin in the Inventive formulas was able to prevent the formation of malondialdehyde after skin samples were exposed to UV light and that it was very effective.

While the disclosure has been described with reference to described embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is "At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

The terms "weight percent" and "wt %" may be used interchangeably and mean percent by weight, based on the total weight of a composition, article or material, except as may be specified with respect to, for example, a phase, or a system that is a component of a composition, article or material. All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cosmetic composition comprising:
   a) about 0.1 to about 1.8 wt. % of *Silybum Marianum* Extract;
   b) about 0.1 to about 2 wt. % of salicylic acid;
   c) about 2 to about 20 wt. % of ascorbic acid;
   d) one or more surfactants including alkoxylated fatty alcohols;
   e) from about 3 to about 10 wt. % of Propylene Glycol;
   f) from about 10 to about 18 wt. % of Dipropylene Glycol; and g) water; and wherein the composition has a pH not higher than about 5; and wherein all percentages by weight are based on the total weight of the cosmetic composition.

2. The composition of claim 1, wherein the weight ratio of Propylene glycol to Dipropylene Gycol is about 1:6 to about 1:1.

3. The composition of claim 1, further comprising a glycol other than Propylene Glycol or Dipropylene Glycol and chosen from ethylene glycol, butylene glycol, hexylene glycol, pentylene glycol, 1,3-propanediol, diethylene glycol, caprylyl glycol, glycerin, and a mixture thereof.

4. The composition of claim 1, wherein the one or more surfactants including alkoxylated fatty alcohols is present from about 1 to about 10 wt. % based on the total weight of the cosmetic composition.

5. The composition of claim 1, wherein the composition demonstrates solubility and stability of the *Silybum Marianum* Extract at temperatures in the range from about 5° C. to about 45° C.

6. The composition of claim 1, wherein the water is present from about 35 to about 90 wt. % based on the total weight of the cosmetic composition.

7. A method of preventing or minimizing lipoperoxidation activity on skin, the method comprising applying a cosmetic composition comprising:

a) about 0.1 to about 1.8 wt. % of *Silybum Marianum* Extract;

b) about 0.1 to about 2 wt. % of salicylic acid;

c) about 2 to about 20 wt. % of ascorbic acid;

d) one or more including alkoxylated fatty alcohols;

e) from about 3 to about 15 wt. % of Propylene Glycol;

f) from about 8 to about 18 wt. % of Dipropylene Glycol; and g) water; and wherein the composition has a pH not higher than about 5; and wherein all percentages by weight are based on the total weight of the cosmetic composition.

8. A method for treating skin comprising applying a cosmetic composition of claim 1 to the skin.

* * * * *